(12) United States Patent
Chen et al.

(10) Patent No.: US 11,661,448 B2
(45) Date of Patent: May 30, 2023

(54) NANO-ANTIBODY AND ITS APPLICATION BASED ON SARS-COV-2 S PROTEIN S1 SUBUNIT

(71) Applicant: Shihezi University, Shihezi (CN)

(72) Inventors: Chuangfu Chen, Shihezi (CN); Peng Wu, Shihezi (CN); Chencheng Xiao, Shihezi (CN); Chengyao Li, Shihezi (CN); Yong Wang, Shihezi (CN); Zhen Wang, Shihezi (CN)

(73) Assignee: Shihezi University, Shihezi (CN)

( * ) Notice: Subject to any disclaimer, the term of this patent is extended or adjusted under 35 U.S.C. 154(b) by 102 days.

(21) Appl. No.: 17/371,155

(22) Filed: Jul. 9, 2021

(65) Prior Publication Data

US 2022/0089692 A1    Mar. 24, 2022

(30) Foreign Application Priority Data

Sep. 22, 2020  (CN) .......................... 202011001278.2
Apr. 30, 2021  (CN) .......................... 202110483452.X

(51) Int. Cl.
*C07K 16/10*     (2006.01)
*C12N 15/70*     (2006.01)

(52) U.S. Cl.
CPC .............. *C07K 16/10* (2013.01); *C12N 15/70* (2013.01); *C07K 2317/569* (2013.01); *C07K 2317/92* (2013.01)

(58) Field of Classification Search
None
See application file for complete search history.

(56) References Cited

U.S. PATENT DOCUMENTS

2022/0089693 A1*  3/2022  Chen ...................... C07K 16/10

FOREIGN PATENT DOCUMENTS

| CN | 111592595 A | 8/2020 |
| CN | 111875700 A | 11/2020 |
| CN | 112076315 A | 12/2020 |
| CN | 112390879 A | 2/2021 |

* cited by examiner

*Primary Examiner* — Jeffrey Stucker
*Assistant Examiner* — Selam Berhane
(74) *Attorney, Agent, or Firm* — Nitin Kaushik

(57) ABSTRACT

A nanobody and its application based on SARS-CoV-2 S protein S1 subunit are provided, and the present disclosure relates to biomedical technology. The present disclosure chooses the Spike RBD of SARS-CoV-2 as a target, and screens the nanobody targeting SARS-CoV-2 by using a nanobody library. After an ELISA test, the Spike RBD target of SARS-CoV-2 can be specifically identification while a SPIKE S1+S2 ECD target is identification, and a binding signal is relatively strong. The corresponding nanobody sequence is constructed into a prokaryotic expression vector for expression and purification to express the target nanobody successfully. After purification, the purity is greater than 90%. The ELISA test of VHH nanobody showed that the purified nanobody has higher affinity to the two targets.

10 Claims, 8 Drawing Sheets

Specification includes a Sequence Listing.

>pET28a-SUMO-(SPIKE S1+S2 ECD)-22 ( His-SUMO-sdAb-HA tag )

DNA

ATGGGCAGCAGCCATCATCATCATCATCACAGCAGCGGCCTGGTGCCGCGCGGCAGCCATATGGC
TAGCATGTCGGACTCAGAAGTCAATCAAGAAGCTAAGCCAGACGTCAAGCCAGAAGTCAAGCCTG
AGACTCACATCAATTTAAAGGTGTCCGATGGATCTTCAGAGATCTTCTTCAAGATCAAAAAGACC
ACTCCTTTAAGAAGGCTGATGGAAGCGTTCGCTAAAAGACAGGGTAAGGAAATGGACTCCTTAAG
ATTCTTGTACGACGGTATTAGAATCCAAGCTGATCAGACCCCTGAAGATTTGGACATGGAGGATA
ACGATATTATTGAGGCTCACAGAGAACAGATTGGTGGATCCCAGGTGCAGCTGCAGGAGTCTGGA
GGAGGCTTGGTGCAGGCTGGAGGGTCTCTGAGACTCTCTTGTGCCGCCAGCGGACGTACTTTCTC
TTCTAACGCTATGGGCTGGTTCCGCCAGGCTCCAGGGAAGGAGCGTGAGTTCGTAGCAGCGATTT
CTTCTGGTTCTGGTTCTACTAACTATGCAGACTCCGTGAAGGGCCGATTCACCATCTCCAGAGAC
AACGCCAAGAACACGGTGTATCTTCAAATGAACAGCCTGAAACCTGAGGACACGGCCGTTTATTA
CTGTGCAGCCGCTTACCGTTACAACGGTCGTGACTACTACGACCGTTACGACTACTGGGGTCAGG
GTACTCAGGTCACCGTCTCCTCAGCGGCCGCATACCCGTACGACGTTCCGGACTACGGTTCCTGA
CTCGAG protein

MGSSHHHHHHSSGLVPRGSHMASMSDSEVNQEAKPEVKPEVKPETHINLKVSDGSSE
IFFKIKKTTPLRRLMEAFAKRQGKEMDSLRFLYDGIRIQADQTPEDLDMEDNDIIEA
HREQIGGSQVQLQESGGGLVQAGGSLRLSCAASGRTFSSNAMGWFRQAPGKEREFVA
AISSGSGSTNYADSVKGRFTISRDNAKNTVYLQMNSLKPEDTAVYYCAAAYRYNGRD
YYDRYDYWGQGTQVTVSSAAAYPYDVPDYGS*

FIG.6

NANO-ANTIBODY AND ITS APPLICATION BASED ON SARS-COV-2 S PROTEIN S1 SUBUNIT

CROSS-REFERENCE TO RELATED APPLICATIONS

The application claims priority to Chinese patent application No. 2020110012782, filed on Sep. 22, 2020, the entire contents of which are incorporated herein by reference.

TECHNICAL FIELD

The present disclosure relates to biomedical technology, in particular to a nanobody and its application based on SARS-CoV-2 S protein S1 subunit.

BACKGROUND

2019 Novel Coronavirus (2019-nCoV) is a kind of virus with a spherical shape, a protruding surface and a crown-like appearance observed under an electron microscopy, and the virus gene is a continuous linear single-stranded RNA with a diameter of 75-160 nm. International Committee on Taxonomy of Viruses stated that the 2019 Novel Coronavirus is officially renamed severe acute respiratory syndrome coronavirus 2, namely SARS-CoV-2. According to a press conference of the Joint Prevention and Control Mechanism of the State Council, the pneumonia infected with the novel coronavirus is uniformly named the Novel Coronavirus Pneumonia, NCP for short. World Health Organization (WHO) announced that the 2019 Novel Coronavirus is named COVID-19, wherein CO stands for corona, VI stands for virus, D stands for disease, the number 19 stands for the year when the disease was found. Common signs of the people infected with SARS-CoV-2 include respiratory tract symptoms, fever, cough, shortness of breath and dyspnea, and so on. Among the severe cases, the infection can cause pneumonia, severe acute respiratory syndrome, renal failure, and even death.

SARS-CoV-2 genome encodes spike protein, envelope protein, membrane protein and nucleocapsid in sequence. S protein (spike protein) is the most important surface membrane protein of the coronavirus and contains two subunits, namely S1 and S2. S1 mainly includes a receptor binding domain, responsible for identifying the receptors of the cell. S2 contains the essential elements needed for membrane fusion. S1 subunit can be further divided into two relatively independent domains, namely N-terminal domain (NTD) and C-terminal domain (CTD). S1 contains the receptor binding domain (RBD), most of receptor binding domains of SARS-CoV S protein are located in the C-terminal domain, such as SARS-CoV and MERS-CoV, and so on. Only a few receptor binding domains of β coronavirus are located in the N-terminal domain (N-terminal domain usually binds a carbohydrate receptor, C-terminal domain binds a protein receptor). S2 subunit is anchored into a membrane through a transmembrane domain and contains the essential elements needed for the membrane fusion process, comprising a fusion peptide (FP), two heptad repeats (HR), a juxtamembrane domain (JMD), a transmembrane domain (TMD) and a cytoplasmic domain (CD). S protein is a vital action site for a host to neutralize the nanobody. S protein is the key target of vaccine design: all coronaviruses possess a conservative function of motif, respectively located in the domain of S1 (the receptor binding domain sequence is highly conservative) and S2 (S2 is more conservative than the amino acid sequence in the domain of S1), and the studies of receptor binding domain and the domain of S2 are conducive to designing viral vaccines and developing new anti-coronavirus drugs.

Nanobody, also known as single domain heavy chain antibody, is a special variable domain of heavy chain antibody and possesses a potential of becoming an excellent blocker. Nanobody is the first time to be found in the blood of a camel, besides, it exists in animals, such as alpacas and sharks, and so on. Since the binding modes and binding sites of the nanobodies and antibodies, such as monoclonal antibody, are different, binding to antigens in some special targets is superior to binding to monoclonal antibodies. Nanobody can be expressed by using an expression system, such as prokaryotic cells, and can greatly reduce the production cost of the nanobody. Nanobody can be gene-edited and modified to achieve a better effect. Nanobody does not easily cause the immune response of body, and can be well used as a nanobody application.

Specific nanobody is obtained by screening a phage library of nanobody. The phage library of nanobody is divided into an immune library and a non-immune library. The immune library is prepared by using camels and other animals that contain immunizing alpacas. The non-immune library is prepared by random editing of the variable domain while retaining a certain constant domain, according to the structure of the constant and the variable domain of the nanobody. When the storage capacity of the nanobody library reaches over $10^7$, the specific nanobody targeting the antigen can be obtained. The usage of the non-immune library saves time and avoids harm to collection of the blood of immunized animals.

At present, SARS-CoV-2 has spread rapidly all over the world, endangered the life security of human beings, and disrupted the worldly economy. Therefore, it is urgent to research and develop the nanobody targeting SARS-CoV-2.

SUMMARY

In light of the problems of the prior art, the present disclosure provides a nanobody and its application based on SARS-CoV-2 S protein S1 subunit in order to solve some problems existing in the prior art or at least mitigate them in the prior art.

The disclosure is realized as follows: the nanobody targeting SARS-CoV-2 S protein S1 subunit, comprising: a single domain antibody protein, sdAb, fragment, and an amino acid sequence of the sdAb fragment is shown in SEQ ID NO.6.

Further, a nucleotide sequence of the sdAb fragment is shown in SEQ ID NO.6.

An expression vector, comprising the nucleotide sequence as described above.

Further, the amino acid sequence of the expression vector is shown in SEQ ID NO.2.

Further, the nucleotide sequence of the expression vector is shown in SEQ ID NO.1.

A host expression strain, comprising the expression vector as described above.

Further, the vector is a prokaryotic expression vector.

Further, the disclosure provides a method for preparing the nanobody based on SARS-CoV-2 S protein S1 subunit, comprising:

inserting the nucleotide sequence encoding the nanobody between a restriction enzyme cutting site of BamHI and a restriction enzyme cutting site of XhoI of a pET28a-SUMO expression vector to obtain the expression vector;

transforming the expression vector into a bacterial strain of *E. coli* BL21 (DE3), and selecting monoclonal colonies for extended culture;

collecting and purifying the nanobody protein by cell breaking, after an induced expression.

Further, 6×His tag is added to N terminal of the pET28a-SUMO expression vector SUMO.

Further, the disclosure provides the application of the nanobody based on SARS-CoV-2 S protein S1 subunit or expression vectors for preparing an agent for the treatment and/or diagnosis of SARS-CoV-2 infection.

The disclosure has the following advantages and beneficial effects:

The disclosure chooses the structure of Spike RBD protein on the SARS-CoV-2 as a target, and screens a prefabricated nanobody library to obtain the nanobody at the phage level. The nanobody targeting SARS-CoV-2, screened by the disclosure, can specially identify the Spike RBD target of SARS-CoV-2, while it can identify the SPIKE S1+S2 ECD target through the ELISA test, and the binding signal is relative strong. The corresponding nanobody sequence is constructed into the prokaryotic expression vector for expression and purification to express the target nanobody successfully, and the purity is greater than 90% after purification; and then through ELISA test of VHH nanobody (VHH is a simplified form of nanobody), it is found that the purified nanobody has higher affinity to the two targets.

Since the Spike S1+S2 ECD protein contains the Spike RBD protein, the nanobody bound to one of the targets can also be bound to the other. The two kinds of targets possess different sizes and locations while the used expression systems are different, which fully illustrate the binding force of the nanobody targeting SARS-CoV-2.

Further, the inventor uses pseudovirus to illustrate that the nanobody blocks the cells infected with SARS-CoV-2, and also illustrate that the nanobody possesses the ability to bind SARS-CoV-2 and to hinder SARS-CoV-2 to infect the cells; the ability of the nanobody to bind the virus neutralizing site is verified by using a SARS-CoV-2 Surrogate Virus Neutralization Test Kit from GenScript.

BRIEF DESCRIPTION OF DRAWINGS

FIG. 6 is a sequence of a nanobody;

DETAILED DESCRIPTION OF THE EMBODIMENTS

For a better understanding of the objects, technical solutions, and advantages of the present application, the disclosure is further illustrated with the following embodiments, and the equipment and reagents used in each embodiment and test with no specific explanation can be obtained from commercial channels. The specific embodiments described here are only used to explain the disclosure, and are not used to limit the application.

According to the information included in the application, it is easy for the technical personnel in the field to make other modification of the precise description of the application, without deviating from the spirit and scope of the claims. Notice that the defined process, nature and component are not intended to limit the scope of the application since the embodiments and other description are only to indicatively illustrate the specific aspect of the present application. Indeed, any modification, equivalent replacement, and improvement made by the persons skilled in the field or any related fields shall be included in the protection scope of the claims.

The specific descriptions of the present application are shown in the embodiments as follows.

EMBODIMENTS

1. Selection of Target Protein

The target protein used in the embodiment of the application is SARS-CoV-2 Spike RBD-His Recombinant Protein purchased from Sino Biological Inc. (No: 40592-V08B, 20 kd, 293 cell expressions, code: Spike RBD).

2. Selection of the Nanobody Library:
using prefabricated nanobody library

1) Brief Introduction to Display System of the Nanobody Library

Figure 1:
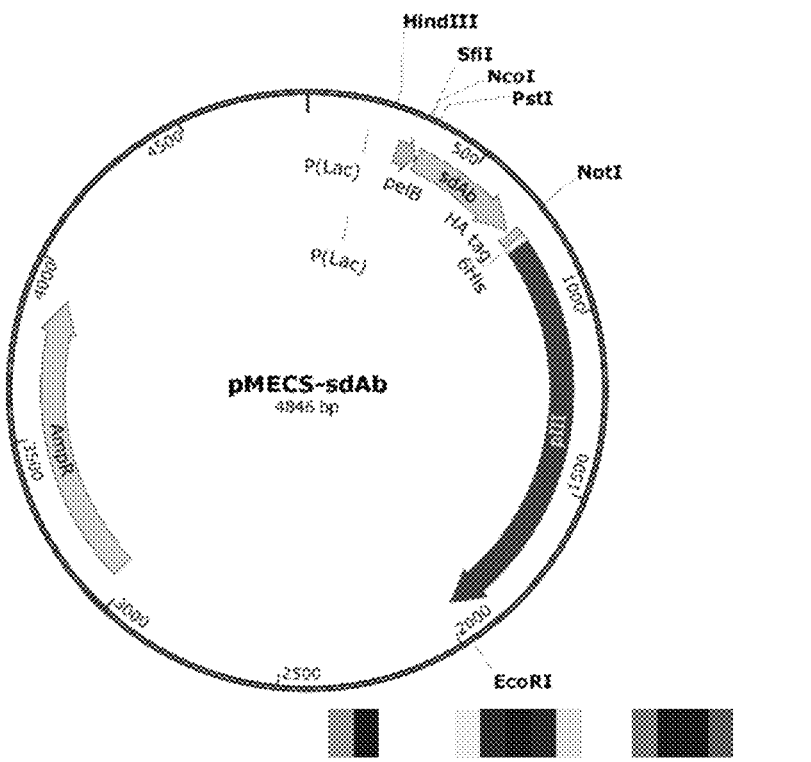
FIG. 1 is a phagemid map of a pMECS-nanobody.
Figure 2:
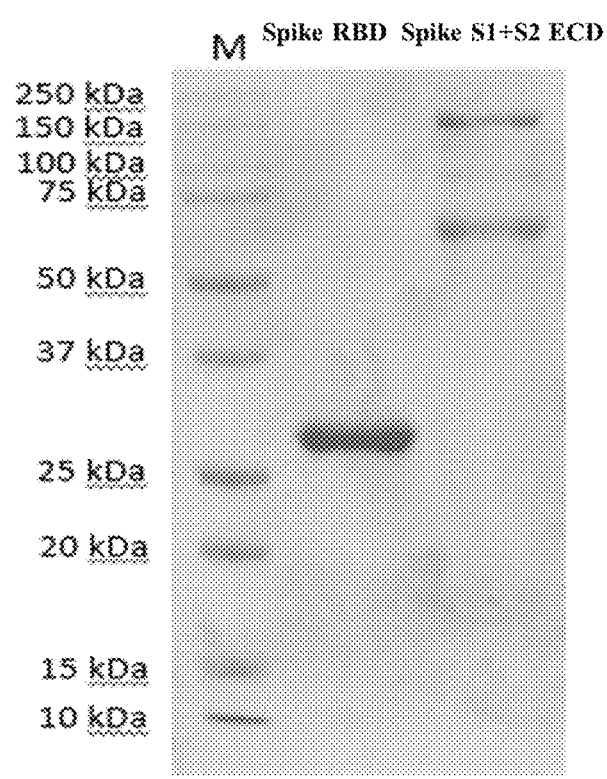
FIG. 2 is an electrophoretic result of a SPIKE S1+S2 ECD protein SDS-PAGE.
Figure 3:
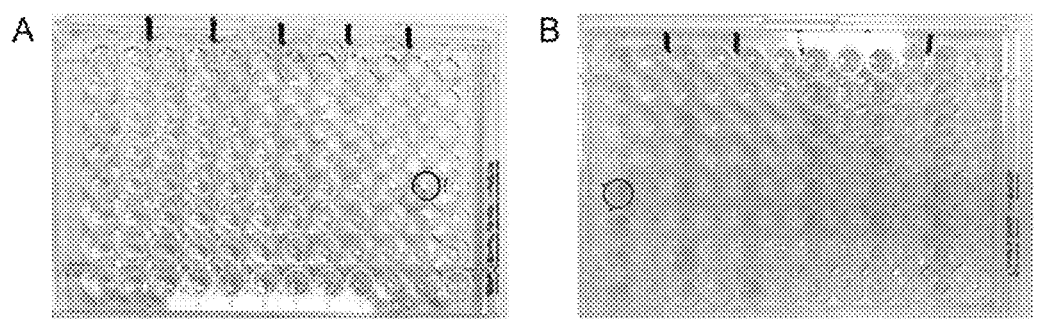
FIG. 3 is a result of an ELISA test of a Monoclonal phage.
Figure 4:
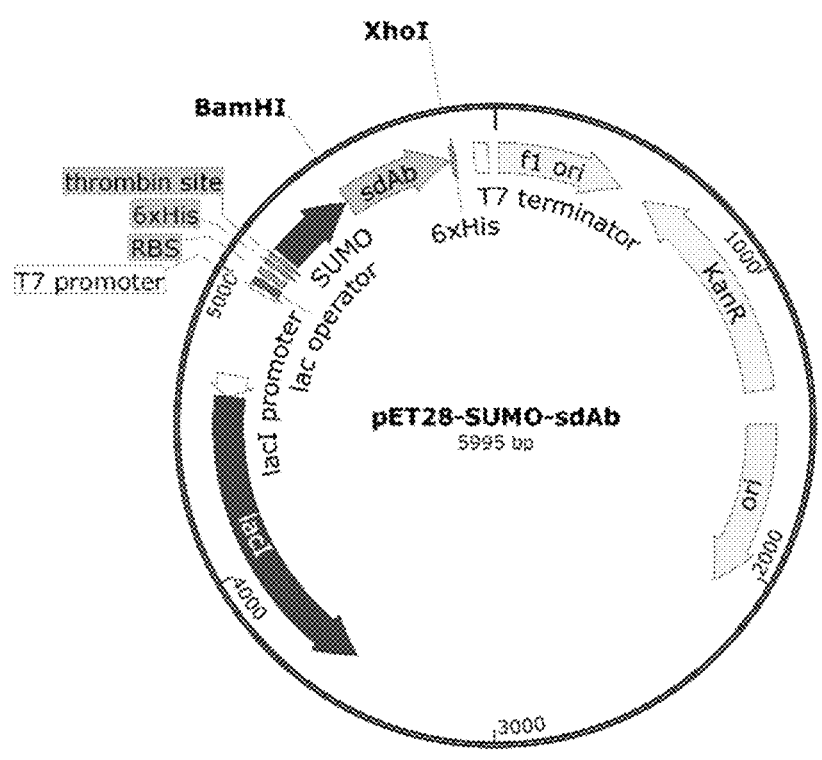
FIG. 4 is a map of a PET28a-SUMO-nanobody vector.
Figure 5:
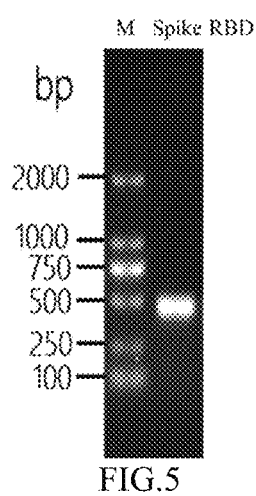
FIG. 5 is an electrophoretic result of PCR amplification product of a nanobody fragment.
Figure 7:
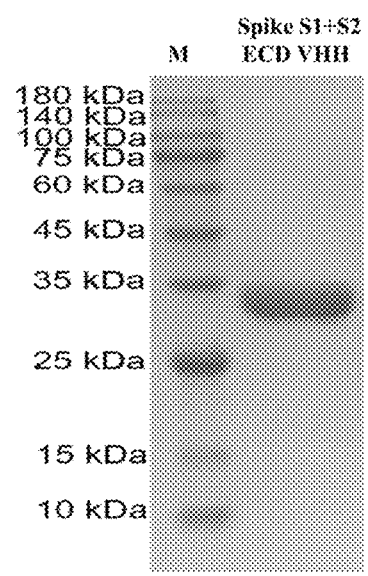
FIG. 7 is an SDS-PAGE analysis of a SUMO-nanobody sample.
Figure 8:
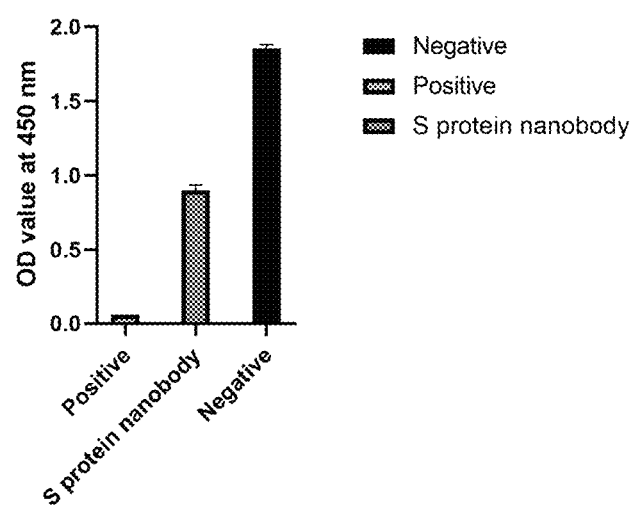
FIG. 8 is an experimental result of detecting neutralizing activity of the nanobody by a SARS-CoV-2 neutralizing antibody ELISA test kit.

The nanobody library is a library constructed by M13 phage display system, which comprises pMECS phagemid vector, *E. coli* TG1 and M13KO7 auxiliary phage. The structure of the pMECS bacteriophage carrier is shown in FIG. 1: the previous sequence of Pst I restriction enzyme cutting site is the coding sequence of pelB secretory signal peptide and partial amino acids in the first frame domain of the nanobody, after the pelB signal peptide successfully guiding the subsequent nanobody to the periplasmic cavity, the signal peptide enzyme works on the end of AQPAMA sequence and removes the pelB signal peptide; the coding sequences of HA and 6×His tag behind Not I restriction enzyme cutting site can be used for purification or detection of fusion proteins. The following encoding sequence is phage pIII capsid protein. There is an amber termination codon between 6×His tag and the gene III sequence, 10%-20% amber terminator codon can be translated into glutamate (Glu, or E) in amber terminator codon-inhibiting strain (For example: *E. coli* TG1), and causes the binding of the nanobody and pIII protein. When rescued by the auxiliary phage M13KO7, the nanobody is displayed at the N-terminal of pIII protein at the tail of phage.

3. Screening and Identification of the Nanobody

1) Analysis of Target Proteins by SDS-PAGE

Denaturing 3 μg SPIKE RBD, and then adding 10% SDS-PAGE gel to 3 μg SPIKE RBD for electrophoresis analysis. The results are shown in Table 2: SPIKE RBD has a main band with a molecular weight around 30 kDa; the sample does not degrade, and the purity also meets the screening requirements.

2) Screening Strategy and Potency is MP57 (TTATGCTTCCGGCTCGTATG). And then analyzing and arranging the sequencing sequences to obtain the unique VHH nanobody sequence. The results are shown in SEQ ID NO.6.

TABLE 1

Screening method of the nanobody of the SPIKE RBD protein

| Times of screening | Screening conditions | Numbers of phages filtered in | Number of phages screened out | Multiples of enrichment |
|---|---|---|---|---|
| first round of screening | target protein: SPIKE RBD (10 μg) confining liquid: 2% Milk-PBS washing condition: 0.1% Tween20-PBS, 10 cycles elution requirement: 0.2M Glycine-HCl, pH 2.2 buffer: 2% Milk | $1.0 \times 10^{13}$ | $2.2 \times 10^{6}$ | $4.5 \times 10^{6}$ |
| second round of screening | target protein: SPIKE RBD (10 μg) confining liquid: 2% Milk-PBS washing condition: 0.1% Tween20-PBS, 12 cycles elution requirement: 0.2M Glycine-HCl, pH 2.2 buffer: 2% Milk | $2.1 \times 10^{12}$ | $3.1 \times 10^{8}$ | $6.7 \times 10^{3}$ |
| second round of screening | target protein: blank control group confining liquid: 2% Milk-PBS washing condition: 0.1% Tween20-PBS, 12 cycles elution requirement: 0.2M Glycine-HCl, pH 2.2 buffer: 2% Milk | $2.1 \times 10^{12}$ | $1.4 \times 10^{8}$ | $1.5 \times 10^{4}$ |
| third round of screening | target protein: SPIKE RBD (10 μg) confining liquid: 2% Milk-PBS washing condition: 0.1% Tween20-PBS, 15 cycles elution requirement: 0.2M Glycine-HCl, pH 2.2 buffer: 2% Milk | $2.2 \times 10^{12}$ | $3.3 \times 10^{9}$ | $6.6 \times 10^{2}$ |
| third round of screening | target protein: blank control group confining liquid: 2% Milk-PBS washing condition: 0.1% Tween20-PBS, 15 cycles elution requirement: 0.2M Glycine-HCl, pH 2.2 buffer: 2% Milk | $2.2 \times 10^{12}$ | $4.6 \times 10^{5}$ | $4.6 \times 10^{4}$ |
| fourth round of screening | target protein: SPIKE RBD (10 μg) confining liquid: 2% Milk-PBS washing condition: 0.1% Tween20-PBS, 20 cycles elution requirement: 0.2M Glycine-HCl, pH 2.2 buffer: 2% Milk | $2.1 \times 10^{12}$ | $4.6 \times 10^{9}$ | $4.5 \times 10^{2}$ |
| fourth round of screening | target protein: blank control group confining liquid: 2% Milk-PBS washing condition: 0.1% Tween20-PBS, 20 cycles elution requirement: 0.2M Glycine-HCl, pH 2.2 buffer: 2% Milk | $2.1 \times 10^{12}$ | $2.7 \times 10^{6}$ | $7.7 \times 10^{4}$ |

3) ELISA Results of the SPIKE RBD Monoclonal Phage

Selecting three monoclonal colonies randomly from the Output clone after the third round of screening of SPIKE RBD. After conducting the phage rescue, performing the of the monoclonal phage ELISA test for three monoclonal colonies in the ELISA wells coated with the SPIKE RBD target (200 ng/well), comparing to No Coating. The detailed results are shown in Table 2, there are three specific identification targets of SPIKE RBD in R3 clone.

TABLE 2

ELISA results of the SPIKE RBD monoclonal phage of R3 clone

| Clone | Coated SPIKE RBD protein | Blank comparison |
|---|---|---|
| 1 | 1.0034 | 0.0492 |
| 2 | 1.9415 | 0.048 |
| 3 | 1.4305 | 0.0525 |
| M13KO7 | 0.0434 | 0.047 |
| 1% M-PBS | 0.0436 | 0.0453 |

4) Sequence Analysis of Positive Clones

Sequencing the clones of specific identification target protein screened by SPIKE RBD, and the sequencing primer 5) Soluble ELISA Experiment of Positive Clones Performing IPTG induced expression for the clones of the specific identification SPIKE RBD (in *E. coli* TG1) at 30° C., and collecting the bacterial cells after centrifugation to do extraction from periplasmic cavity. Diluting the sample extracted from periplasmic cavity 10 times with 0.5× blocker for reserve. Coating the SPIKE RBD target (200 ng/well) on the 96-well ELISA plate, and detecting the samples extracted from the diluted periplasmic cavity by ELISA, comparing to No Coating. Anti-HA mouse McAb is a secondary antibody of ELISA test, and HRP-conjugated Goat Anti-Mouse IgG (H+L) is a tertiary antibody. The results are shown in Table 3, and the clones can bind the target proteins specifically.

TABLE 3

ELISA experiment for binding the nanobody to the SPIKE RBD protein in phage

| Group | Coated SPIKE RBD | Blank comparison |
|---|---|---|
| OD450 | 2.2712 | 0.0546 |

6) Performing ELISA Test for the SPIKE S1+S2 ECD Target

The S protein of SARS-CoV-2 (2019-nCoV) SPIKE S1+S2 ECD-His Recombinant Protein (Item No. 40589-V08B1, full length extracellular segment, 130 kd, insect cell expression, code: Spike S1+S2 ECD), purchased from Sino Biological Inc., is used for ELISA test in the embodiment case of the application.

The periplasmic cavity of the clones binding to the SPIKE S1+S2 ECD target is used to extract the samples, and detecting the SPIKE S1+S2 ECD target by ELISA. The detecting method is the same as the soluble ELISA. The results are shown in Table 4: The clones that can identify SPIKE RBD can also identify the SPIKE S1+S2 ECD target, and the binding signal is relatively strong.

TABLE 4

ELISA experiment for binding nanobody to SPIKE S1 + S2 ECD protein in phage

| Group | Coated SPIKE S1 + S2 ECD proteins | Blank comparison |
|---|---|---|
| OD450 | 2.3514 | 0.0715 |

4. The ELISA Test of the Monoclonal Phage after Screening

The ELISA method coating: diluting the target protein to 2 μg/mL with 1×PBS pH 7.4, adding target protein to the ELISA plate hole 100 μL/well, and coating the ELISA plate overnight at 4° C.;

blocking: washing the ELISA plate with PBST (0.1% Tween) for one time, adding to 300 μL 5% BSA each well as the confining liquid, and incubating the ELISA plate for 2 hours at 37° C.;

incubating phage supernatant: washing the ELISA plate with PBST (0.1% Tween) for one time, and adding 100 μL of phage supernatant to the corresponding ELISA well, and incubating the ELISA plate for 2 hours at 37° C.;

incubating and detecting the nanobody: washing the ELISA plate with PBST (0.1% Tween) for three times, and diluting anti-M13-HRP (1:5000) with 2.5% BSA. Adding anti-M13-HRP to the corresponding ELISA plate 100 μL/well, and incubating the ELISA plate for 1 hour at 37° C.;

TMB color development: washing the plate with PBST (0.1% Tween) for 3 times, and washing the plate with PBS for 2 times, starting TMB color development under 100 μL/well, incubating the ELISA plate for about 30 minutes at 37° C. until 2 M $H_2SO_4$ is 50 μL/well;

reading enzyme calibration: detecting light absorption value at OD450 nm by using the enzyme calibration.

2) Results of Detection

The results are shown in Table 3, wherein A: the detection of the SPIKE RBD target, B: the detection of the SPIKE S1+S2 ECD target.

5. Acquisition of the Nanobody

1) Construction and Purification of the Prokaryotic Expression Vector of Positive Clones SUMO tag protein is a small ubiquitin-like modifier with a molecular weight of about 11.2 kDa. As a fusion tag for recombinant protein expression, SUMO tag can increase the weight of expression of fusion protein, with antiprotease hydrolysis, and can promote the correct folding of target protein and improve the solubility of recombinant protein. To obtain soluble expression of the nanobody, inserting the coding sequence of the nanobody between a restriction enzyme cutting site of BamHI and a restriction enzyme cutting site of XhoI of an expression vector pET28a-SUMO to make the coding sequence of the nanobody conduct fusion expression with SUMO tag, and the N terminal of SUMO, added with 6×His tag, can be used to purify the fusion protein, while the C terminal of the nanobody, added with HA tag, can be used to detect. The vector map of the pET28a-SUMO-nanobody is shown in Table 4.

Inoculating the clones (pMECS in TG1) that identifies SPIKE RBD into the 2YT-AG medium and culturing the clones overnight at 37° C., the cloned bacterial solution is used as a model and SUMOVHH-F and SUMOVHH-R are used as primers.

TABLE PCR system

| PCR system | |
|---|---|
| Model | 1-2 μL |
| 10 X NovaTaq confining liquid, contains $MgCl_2$ | 5 μL |
| SUMOVHH-F (5 pmol/μL) | 1 μL |
| SUMOVHH-R (5 pmol/μL) | 1 μL |
| 10 mM: dATP, dCTP, dGTP, dTTP | 1 μL |
| DNA polymerase | 1.25 U |

| PCR reaction condition | | |
|---|---|---|
| reaction condition | | |
| 95° C. | 5 min | 1 cycle |
| 94° C. | 50 s | |
| 55° C. | 1 min | 35 cycles |
| 72° C. | 1 min | |
| 72° C. | 6 min | 1 cycle |

Amplifying the gene fragment of the nanobody by PCR, the agarose gel electrophoresis results of PCR product are shown in Table 5: the fragment is effectively amplified, and the size of the fragment is about 400 bp, the results are consistent with expectation. Adding the PCR product to 1.2% agarose gel for electrophoresis separation respectively, and purifying the target fragment by gel cutting and recovering the target fragment by using a gel extraction kit.

```
SUMOVHH-F:
cacagagaacagattggtggatccCAGGTGCAGCTGCAGG,
as seen in SEQ ID NO. 3.

SUMOVHH-R:
cagtggtggtggtggtggtgctcgagtcaGGAACCGTAGTCCGGAAC,
as seen in SEQ ID NO. 4.
```

Synthesizing the nanobody into pET28a-SUMO expression plasmid.

The expression cassette sequence of SUMO-nanobody is shown in SEQ ID NO.1, the amino acid sequence is shown in SEQ ID NO.2; as shown in Table 6, the structural domains of His, SUMO, the nanobody and HA tag are distinguished by using different gray intensity and underscores, and correspond to the gray intensity and underscores of the names.

Transforming the expression vector of the SPIKE RBD SUMO-nanobody into E. coli BL21 (DE3) strain, and coating the Kan-resistant plate. After overnight culture, picking out the monoclonal colonies and inoculating it into the 200 mL 2YT-K medium, and culturing the plate until the middle of the logarithmic growing period, then adding 1 m M final density of IPTG solution, and inducing the plate overnight at 30° C. Collecting the bacterial precipitation by centrifugation, and after breaking the bacterial cells by ultrasonic wave, purifying SUMO-nanobody by Ni ion affinity chromatography column, concentrating the sample by Millipore concentration tube and placing the buffer into PBS (pH7.4). Filtering the bacteria with the 0.22 μm filter membrane, adding 5% the final density of the sterile glycerol, freezing the sample after packing. Conducting quantitative analysis for the sample of purified SUMO-nanobody through using Nanodrop, the results are shown as Table 6. Finally, detecting the above sample by SDS-PAGE electrophores, the results are shown as Table 5: the purified sample of SPIKE RBD ECD SUMO-nanobody only has a target band near 28 kDa, the purity is greater than 90%.

TABLE 5

Information of the sample density

| Item | Description | Volume | Concentration | Quantity |
|---|---|---|---|---|
| 1 | SPIKE RBD nanobody | 2.9 ml | 1.35 mg/mL | 3.92 mg |

6. ELISA Test of VHH Nanobody

Coating the SPIKE S1+S2 ECD target and the SPIKE RBD target (200 ng/well) respectively on the 96-well ELISA plate to verify the specificity and affinity of SPIKE RBD SUMO-nanobody, comparing to No Coating, and conducting concentration gradient ELISA test for SPIKE RBD SUMO nanobody, Anti-HA mouse McAb is the secondary antibody of ELISA test, and HRP-conjugated Goat Anti-Mouse IgG (H+L) is the third antibody. The results are shown as Table 6: SUMO-nanobody has the binding activity to both targets (SPIKE S1+S2 ECD and SPIKE RBD).

TABLE 6

Results of the ELISA test for SUMO-nanobody

| Nanobody density(ng/mL) | | 3000 | 1000 | 333.333 | 0 |
|---|---|---|---|---|---|
| SPIKE RBD | SPIKE S1 + S2 ECD | 0.3381 | 0.211 | 0.1783 | 0.0821 |
| | SPIKE RBD | 0.5639 | 0.2903 | 0.2113 | 0.0675 |
| | No Coating | 0.0812 | 0.0641 | 0.0663 | 0.056 |

7. Detecting the Experiment on the Neutralizing Activity of the Nanobody by a SARS-CoV-2 Neutralizing Antibody ELISA Test Kit Using the SARS-CoV-2 neutralizing antibody ELISA test kit from Jiangsu GenScript Biotechnology Co., Ltd. to detect the experiment on the neutralizing activity of the nanobody in the embodiment. The specific operations are as follows:

Mixing positive control, negative control and the samples with the solution respectively in advance at 1:1 volume ratio (The positive control is the neutralizing antibody of SARS-CoV-2 carried by L00847 SARS-CoV-2 Surrogate Virus neutralization ation Test Kit from GenScript Biotechnology Co., Ltd.; negative control is the human's IgG). For example, adding 60 μL HRP-RBD solution to 60 μL positive control and incubating the HRP-RBD solution at 37° C. for 30 minutes. Adding 100 μL mixed solutions of positive control, negative control and sample to the enzyme standard plate. After covering with a film of cover plate, incubating the plate for 15 minutes at 37° C. Removing the film and washing the cover plate with 260 μL 1× cleansing solution for 4 times. After washing, removing the remaining liquid from the hole in the cover plate by using paper towel. Adding 100 μL TMB Solution to each well of the enzyme label plate, and incubating the plate for 10-15 minutes at 20-25° C. in a dark place (start from adding to TMB Solution). Removing the film, and adding 50 μL stopping solution to each well. After stopping, measuring light absorption value at 450 nm by the enzyme calibration immediately.

Result: according to the detecting results of L00847 SARS-CoV-2 Surrogate Virus Neutralization Test Kit, it shows that nanobody has neutralizing activity. The data is shown as Table 8.

8. Detecting the experiment on the neutralizing activity of nanobody by SARS-CoV-2 pseudovirus The pseudovirus is constructed and provided by Li Chengyao of Southern Medical University. The specific operations are as follows:

1) preparing sample: the prepared nanobody determination concentration;

2) adding DMEM complete medium to 100 μL/well of the plate in column 1 (cell control CC), adding DMEM complete medium to 50 μl/well of the plate in column 2 (virus control VC), adding DMEM complete medium to 90 μl/well of the plate in the third column, and adding 50 μl DMEM complete medium to the rest well;

3) adding 10 μL the nanobody sample to be tested;

4) sucking and blowing the liquid in the third column gently and repeatedly for 6-8 times, then transferring 50 μl liquid to the corresponding well, after that, all wells are diluted for twice;

5) diluting the SARS-CoV-2 pseudovirus to $1.28 \times 10^4$ $TCID_{50}$/mL with DMEM complete medium, and adding 50 μl liquid to each well in columns 3-11, namely 640 $TCID_{50}$ per well;

6) incubating the 96-well plate in a cell incubator (37° C., 5% $CO_2$) for 1 hours;

7) digesting ACE2-293T cells, and diluting the ACE2-293T cells to $3 \times 10^5$ cells/mL after incubation for 30 minutes;

8) adding 100 μl cells to each well to make $3 \times 10^4$ cells per well after the end of incubation;

9) culturing the plate in 5% $CO_2$ incubator at 37° C. for 48 hours;

10) sucking and discarding 100 μl supernatant after the end of cultivation, and adding 100 μl Bright-Glo™ luciferase detection reagent (promega); blowing the plate repeatedly and transferring the 200 μl liquid of the plate to the whiteboard after dark reaction at room temperature for 5 minutes;

11) reading Relative Light Unit (RLU) by using the PerkinElmer EnSight multifunctional imaging enzyme-labeling instrument;

12) calculating the neutralizing inhibition rate:

$$\text{Inhibition rate} = \left(1 - \frac{\begin{array}{c}\text{Mean value of light intensity}\\ \text{of the sample group} - CC\\ \text{mean value of blank control}\end{array}}{\begin{array}{c}VC \text{ mean value} -\\ CC \text{ mean value}\end{array}}\right) \times 100\%$$

When the nanobody concentration corresponding to the neutralizing nanobody titer inhibition rate of 50%, calculating the corresponding neutralizing nanobody titers based on the initial concentration of the nanobody and its addition amount.

Result: the nanobody has neutralizing activity to pseudovirus, and the inhibition rate of pseudovirus increases with the growth of concentration. The results are shown in the table below.

TABLE 7

| Inhibition rate of the nanobody targeting pseudovirus | |
|---|---|
| Diluted concentration (μg/ml) | Inhibition rate % |
| 262.96 | 80.05 |
| 131.48 | 77.13 |
| 65.74 | 73.24 |
| 32.87 | 71.66 |
| 16.43 | 69.68 |
| 8.22 | 64.76 |
| 4.11 | 54.16 |
| 2.05 | 49.32 |

The above is only some better embodiments of the application and does not limit the invention. Any modification, equivalent replacement or improvement made within the spirit and principles of the application shall be covered by the protection of the application.

What is claimed is:

1. A nanobody targeting SARS-CoV-2 S protein S1 subunit, comprising: a single domain antibody protein, sdAb, fragment, wherein an amino acid sequence of the sdAb fragment is SEQ ID NO.5.

2. The nanobody targeting SARS-CoV-2 S protein S1 subunit according to claim 1, wherein the nucleotide sequence of the sdAb fragment is SEQ ID NO.6.

3. An expression vector, comprising the nucleotide sequence of claim 2.

4. The expression vector according to claim 3, wherein an amino acid sequence of the expression vector is SEQ ID NO.2.

5. The expression vector according to claim 3, wherein a nucleotide sequence of the expression vector is SEQ ID NO.1.

6. A host expression strain, comprising the expression vector of claim 3, wherein the host expression strain is a bacterial strain.

7. A method for preparing the expression vector of claim 3, further comprising:
   inserting the nucleotide sequence encoding the nanobody between a restriction enzyme cutting site of BamHI and a restriction enzyme cutting site of XhoI of a pET28a-SUMO expression vector to obtain the expression vector;
   transforming the expression vector into a bacterial strain of *E. coli* BL21, and selecting monoclonal colonies for large-scale cultivation;
   collecting and purifying a nanobody protein by cell breaking after an induced expression.

8. The method for preparing the expression vector according to claim 7, wherein 6×His tag is added to N terminal of the pET28a-SUMO expression vector SUMO.

9. An agent for treatment and/or diagnosis of SARS-CoV-2 infection utilizing the nanobody targeting SARS-CoV-2 S protein S1 subunit of claim 1.

10. An agent for treatment and/or diagnosis of SARS-CoV-2 infection utilizing the expression vector of claim 3.

* * * * *

SEQUENCE LISTING

<160> NUMBER OF SEQ ID NOS: 6

<210> SEQ ID NO 1
<211> LENGTH: 780
<212> TYPE: DNA
<213> ORGANISM: Artificial Sequence
<220> FEATURE:
<223> OTHER INFORMATION: Laboratory Synthesized

<400> SEQUENCE: 1

```
atgggcagca gccatcatca tcatcatcac agcagcggcc tggtgccgcg cggcagccat      60
atggctagca tgtcggactc agaagtcaat caagaagcta agccagaggt caagccagaa     120
gtcaagcctg agactcacat caatttaaag gtgtccgatg gatcttcaga gatcttcttc     180
aagatcaaaa agaccactcc tttaagaagg ctgatggaag cgttcgctaa agacagggt      240
aaggaaatgg actccttaag attcttgtac gacggtatta gaatccaagc tgatcagacc     300
cctgaagatt tggacatgga ggataacgat attattgagg ctcacagaga acagattggt     360
ggatcccagg tgcagctgca ggagtctgga ggaggcttgg tgcaggctgg agggtctctg     420
agactctctt gtgccgccag cggatacacc aacagtcgct actacatggg ctggttccgc     480
caggctccag ggaaggagcg tgagttcgta gcagcgattt ctgctattgg tcgcacatac     540
tatgcagact ccgtgaaggg ccgattcacc atctccagag acaacgccaa gaacacggtg     600
tatcttcaaa tgaacagcct gaaacctgag gacacggccg tttattactg tgcagccgac     660
tcttctctgg ctggtctgcg tggtcgtctg tacgactact ggggtcaggg tactcaggtc     720
accgtctcct cagcggccgc atacccgtac gacgttccgg actacggttc ctgactcgag     780
```

<210> SEQ ID NO 2
<211> LENGTH: 257
<212> TYPE: PRT
<213> ORGANISM: Artificial Sequence
<220> FEATURE:
<223> OTHER INFORMATION: Laboratory Synthesized

<400> SEQUENCE: 2

```
Met Gly Ser Ser His His His His His His Ser Ser Gly Leu Val Pro
1               5                   10                  15

Arg Gly Ser His Met Ala Ser Met Ser Asp Ser Glu Val Asn Gln Glu
                20                  25                  30

Ala Lys Pro Glu Val Lys Pro Glu Val Lys Pro Glu Thr His Ile Asn
            35                  40                  45

Leu Lys Val Ser Asp Gly Ser Ser Glu Ile Phe Phe Lys Ile Lys Lys
        50                  55                  60

Thr Thr Pro Leu Arg Arg Leu Met Glu Ala Phe Ala Lys Arg Gln Gly
65                  70                  75                  80
```

```
Lys Glu Met Asp Ser Leu Arg Phe Leu Tyr Asp Gly Ile Arg Ile Gln
                85                  90                  95

Ala Asp Gln Thr Pro Glu Asp Leu Asp Met Glu Asp Asn Asp Ile Ile
            100                 105                 110

Glu Ala His Arg Glu Gln Ile Gly Gly Ser Gln Val Gln Leu Gln Glu
        115                 120                 125

Ser Gly Gly Gly Leu Val Gln Ala Gly Gly Ser Leu Arg Leu Ser Cys
    130                 135                 140

Ala Ala Ser Gly Tyr Thr Asn Ser Arg Tyr Tyr Met Gly Trp Phe Arg
145                 150                 155                 160

Gln Ala Pro Gly Lys Glu Arg Glu Phe Val Ala Ile Ser Ala Ile
                165                 170                 175

Gly Arg Thr Tyr Tyr Ala Asp Ser Val Lys Gly Arg Phe Thr Ile Ser
                180                 185                 190

Arg Asp Asn Ala Lys Asn Thr Val Tyr Leu Gln Met Asn Ser Leu Lys
                195                 200                 205

Pro Glu Asp Thr Ala Val Tyr Tyr Cys Ala Ala Asp Ser Ser Leu Ala
            210                 215                 220

Gly Leu Arg Gly Arg Leu Tyr Asp Tyr Trp Gly Gln Gly Thr Gln Val
225                 230                 235                 240

Thr Val Ser Ser Ala Ala Ala Tyr Pro Tyr Asp Val Pro Asp Tyr Gly
                245                 250                 255

Ser
```

```
<210> SEQ ID NO 3
<211> LENGTH: 40
<212> TYPE: DNA
<213> ORGANISM: Artificial Sequence
<220> FEATURE:
<223> OTHER INFORMATION: Laboratory Synthesized

<400> SEQUENCE: 3
cacagagaac agattggtgg atcccaggtg cagctgcagg                    40

<210> SEQ ID NO 4
<211> LENGTH: 47
<212> TYPE: DNA
<213> ORGANISM: Artificial Sequence
<220> FEATURE:
<223> OTHER INFORMATION: Laboratory Synthesized

<400> SEQUENCE: 4
cagtggtggt ggtggtggtg ctcgagtcag gaaccgtagt ccggaac            47

<210> SEQ ID NO 5
<211> LENGTH: 122
<212> TYPE: PRT
<213> ORGANISM: Artificial Sequence
<220> FEATURE:
<223> OTHER INFORMATION: Laboratory Synthesized

<400> SEQUENCE: 5
```

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Tyr Thr Asn Ser Arg Tyr
            20                  25                  30

Tyr Met Gly Trp Phe Arg Gln Ala Pro Gly Lys Glu Arg Glu Phe Val
        35                  40                  45
```

```
Ala Ala Ile Ser Ala Ile Gly Arg Thr Tyr Tyr Ala Asp Ser Val Lys
    50              55                  60

Gly Arg Phe Thr Ile Ser Arg Asp Asn Ala Lys Asn Thr Val Tyr Leu
 65              70              75                          80

Gln Met Asn Ser Leu Lys Pro Glu Asp Thr Ala Val Tyr Tyr Cys Ala
            85              90                      95

Ala Asp Ser Ser Leu Ala Gly Leu Arg Gly Arg Leu Tyr Asp Tyr Trp
            100             105                 110

Gly Gln Gly Thr Gln Val Thr Val Ser Ser
        115             120

<210> SEQ ID NO 6
<211> LENGTH: 366
<212> TYPE: DNA
<213> ORGANISM: Artificial Sequence
<220> FEATURE:
<223> OTHER INFORMATION: Laboratory Synthesized

<400> SEQUENCE: 6
caggtgcagc tgcaggagtc tggaggaggc ttggtgcagg ctggagggtc tctgagactc       60
tcttgtgccg ccagcggata caccaacagt cgctactaca tgggctggtt ccgccaggct      120
ccagggaagg agcgtgagtt cgtagcagcg atttctgcta ttggtcgcac atactatgca      180
gactccgtga agggccgatt caccatctcc agagacaacg ccaagaacac ggtgtatctt      240
caaatgaaca gcctgaaacc tgaggacacg gccgtttatt actgtgcagc cgactcttct      300
ctggctggtc tgcgtggtcg tctgtacgac tactggggtc agggtactca ggtcaccgtc      360
tcctca                                                                 366
```